United States Patent
Inoo

(10) Patent No.: US 9,833,417 B2
(45) Date of Patent: Dec. 5, 2017

(54) FELBINAC-CONTAINING EXTERNAL PATCH

(75) Inventor: Katsuyuki Inoo, Higashikagawa (JP)

(73) Assignee: Teikoku Seiyaku Co., Ltd., Higashikagawa-shi (JP)

( * ) Notice: Subject to any disclaimer, the term of this patent is extended or adjusted under 35 U.S.C. 154(b) by 0 days.

(21) Appl. No.: 13/882,747

(22) PCT Filed: Nov. 1, 2011

(86) PCT No.: PCT/JP2011/075182
§ 371 (c)(1),
(2), (4) Date: May 30, 2013

(87) PCT Pub. No.: WO2012/060376
PCT Pub. Date: May 10, 2012

(65) Prior Publication Data
US 2013/0236516 A1    Sep. 12, 2013

(30) Foreign Application Priority Data

Nov. 2, 2010   (JP) .................. 2010-246666

(51) Int. Cl.
*A61K 9/70*   (2006.01)
*A61K 31/192*   (2006.01)

(52) U.S. Cl.
CPC .......... *A61K 9/7007* (2013.01); *A61K 9/7053* (2013.01); *A61K 31/192* (2013.01)

(58) Field of Classification Search
None
See application file for complete search history.

(56) References Cited

U.S. PATENT DOCUMENTS

| 5,837,735 | A | * | 11/1998 | Miyata et al. | 514/605 |
| 6,833,138 | B2 | * | 12/2004 | Takada et al. | 424/449 |
| 6,946,514 | B2 | * | 9/2005 | Kawaji | 524/575 |
| 7,094,421 | B2 | | 8/2006 | Akazawa et al. | |
| 2002/0031542 | A1 | | 3/2002 | Takada et al. | |
| 2003/0149383 | A1 | | 8/2003 | Ikeura et al. | |
| 2007/0154531 | A1 | * | 7/2007 | Hashimoto et al. | 424/448 |
| 2009/0074844 | A1 | * | 3/2009 | Nishiura et al. | 424/449 |
| 2011/0165259 | A1 | * | 7/2011 | Hirokawa et al. | 424/498 |

FOREIGN PATENT DOCUMENTS

| JP | 7-233050 A | 9/1995 |
| JP | 10-218793 A | 8/1998 |
| JP | 2001-97857 A | 4/2001 |
| JP | 2001-342130 A | 12/2001 |
| JP | 3541849 B2 | 4/2004 |
| JP | 2007-7189 A | 1/2007 |
| JP | 2007-8927 A | 1/2007 |
| JP | 2007-296120 A | 11/2007 |
| JP | 2008-13494 A | 1/2008 |
| JP | 2008-69127 A | 3/2008 |
| WO | WO 98/24423 A1 | 6/1998 |
| WO | WO 01/78690 A1 | 10/2001 |
| WO | WO 2010/032434 | * 3/2010 |

OTHER PUBLICATIONS

International Search Report with English translation dated Dec. 6, 2011 (five (5) pages).

* cited by examiner

*Primary Examiner* — Richard Schnizer
*Assistant Examiner* — Katherine Peebles
(74) *Attorney, Agent, or Firm* — Crowell & Moring LLP

(57) ABSTRACT

Provided is a felbinac-containing external patch which can exhibit high drug release properties, low skin irritation, and high drug stability, wherein felbinac having an average particle diameter of 5 μm or more and less than 100 μm is dispersed and mixed in an adhesive base including a styrene-isoprene-styrene block copolymer, an alicyclic saturated hydrocarbon resin, a softener, and diethyl sebacate, and does not contain L-menthol. Specifically, in the felbinac-containing external patch, 0.1 to 10% by weight of felbinac having an average particle diameter of 5 μm or more and less than 100 μm is dispersed and mixed in an adhesive base including 10 to 30% by weight of a styrene-isoprene-styrene block copolymer, 10 to 50% by weight of an alicyclic saturated hydrocarbon resin, 10 to 75% by weight of a softener, and 0.1 to 10% by weight of diethyl sebacate.

1 Claim, No Drawings

FELBINAC-CONTAINING EXTERNAL PATCH

TECHNICAL FIELD

The present invention relates to an anti-inflammatory analgesic external preparation having percutaneous absorption properties, and in particular, a felbinac-containing anti-inflammatory analgesic external patch which exhibits good drug release properties, low skin irritation, and high drug stability.

BACKGROUND ART

Felbinac (4-biphenylacetic acid) is an active metabolite of fenbufen which is a non-steroidal anti-inflammatory analgesic agent and also is a drug having high anti-inflammatory analgesic activity. Felbinac has a problem in which oral administration causes side effects in the digestive system, resulting in gastrointestinal injury. Therefore, use of felbinac as a percutaneous absorption preparation has been investigated. To date, external preparations such as a gel preparation and a liquid preparation are commercially available.

In the preparation forms of gel preparation and liquid preparation, quantitative administration is difficult, and bioavailability is low. Further, the preparations have a problem such as adhesion to clothes.

In order to overcome the problems of such gel preparation and liquid preparation, an aqueous patch (cataplasm) and an oily patch (plaster), which contains various anti-inflammatory analgesic agents in addition to felbinac, have been developed. In particular, the oily patch (plaster) becomes the mainstream of a non-steroidal anti-inflammatory analgesic patch since it does not have a cool touch when applied. A preparation having a rubber-based base and a tackifying resin in combination is generally used.

A non-steroidal anti-inflammatory analgesic patch usually contains various additives to improve the percutaneous absorption properties of a drug. In particular, L-menthol is useful as a solvent of felbinac, and is an additive which is often contained in commercially available felbinac-containing patches. However, it is widely known that L-menthol reacts with felbinac to produce an L-menthol ester as a degradation product. Therefore, the presence of L-menthol is a cause of deterioration of felbinac stability in the patch.

Irritating odor produced by sublimation of L-menthol is offensive to many people. For this reason, the market has a high demand for a patch preparation which does not contain L-menthol or prevents L-menthol odor, in fact.

Further, in order to enhance the percutaneous absorption properties of felbinac, addition of a percutaneous absorption enhancer such as crotamiton, fatty acids, fatty acid esters, monoterpenes, polyhydric alcohols, and pyrrolidones has been investigated.

For example, Patent Document 1 has proposed a felbinac-containing patch which has an adhesive layer containing crotamiton having a high solubilizing ability for felbinac as an essential ingredient. However, the patch has a problem of decrease of adhesion with time since crotamiton tends to bleed out onto the surface of the adhesive layer.

Further, Patent Document 2 discloses a felbinac-containing anti-inflammatory analgesic tape which contains a styrene-isoprene-styrene block copolymer as an adhesive and L-menthol and various absorption enhancers in combination. However, L-menthol in the tape may react with felbinac to produce a degradation product as described above. In addition, addition of L-menthol and the absorption enhancer in combination may make physical properties of a base deteriorate and cause skin irritation.

Patent Document 3 also discloses a felbinac-containing patch which contains terpene, sebacate ester, and an alkyl glyceryl ether. However, similarly to Patent Document 2, Patent Document 3 leaves something to be desired in drug stability, physical properties of a base, and skin irritation.

Further, patches containing various percutaneous absorption enhancers, such as a felbinac patch containing N-methyl-2-pyrrolidone and polyethylene glycol in combination (Patent Document 4) and a patch containing hydrogenated oil (Patent Document 5) have been investigated. However, a percutaneous absorption preparation having high percutaneous absorption properties and safety of a drug and excellent drug stability has not been found.

On the other hand, there have been attempts to enhance the percutaneous absorption properties of a drug by a means other than a method for adding a percutaneous absorption enhancer.

For example, Patent Document 6 discloses a water-containing plaster, in which an adhesive base containing a styrene-isoprene-styrene block copolymer as a main component contains lanolin and the lanolin holds water.

The technique disclosed in Patent Document 6 is an attempt to increase the solubility of felbinac by the water content in the preparation, resulting in improvement of percutaneous absorption properties. However, the production process is complicated by incorporating the water content in an oily patch. Further, the physical properties of the preparation during storage may deteriorate.

In addition, the plaster has a problem of slightly lower percutaneous absorption properties as compared with a plaster using a percutaneous absorption enhancer.

Patent Document 7 has proposed a patch. The patch does not contain crotamiton. In the patch, felbinac is uniformly dispersed in an adhesive base containing a styrene-isoprene-styrene block copolymer as a main base and a rosin-based resin.

However, the rosin-based resin in the patch acts as a skin sensitization ingredient. Blending of the rosin-based resin is known to be undesirable. Skin sensitization is one type of delayed-type hypersensitivity reaction, and a phenomenon in which chemicals cause excessive immune reactions to produce irritation to the skin.

PRIOR ART DOCUMENTS

Patent Documents

Patent Document 1: Japanese Patent Application Laid-Open No. Hei 4-321624
Patent Document 2: Japanese Patent Application Laid-Open No. Hei 10-218793
Patent Document 3: Japanese Patent Application Laid-Open No. 2008-13494
Patent Document 4: Japanese Patent Application Laid-Open No. 2001-342130
Patent Document 5: Japanese Patent Application Laid-Open No. 2007-8927
Patent Document 6: Japanese Patent Application Laid-Open No. 2001-97857
Patent Document 7: International Publication WO 98/24423

SUMMARY OF THE INVENTION

Problems to be Solved by the Invention

The present invention has been made to solve the problems. An object of the present invention is to provide a felbinac-containing external patch which can exhibit high drug release properties without L-menthol which is an excellent solvent for felbinac, low skin irritation, and high drug stability.

Means for Solving the Problem

The present inventor has intensively studied to solve the problems. As a result, the inventor has found that when felbinac having an average particle diameter of 5 μm or more and less than 100 μm is dispersed and mixed in an adhesive base including a styrene-isoprene-styrene block copolymer, an alicyclic saturated hydrocarbon resin, a softener, and diethyl sebacate, and does not contain L-menthol, an external patch which exhibits low skin irritation, and excellent drug release properties and drug stability of felbinac is obtained. Thus, the present invention has been completed.

A basic aspect of the present invention is a felbinac-containing external patch wherein felbinac having an average particle diameter of 5 μm or more and less than 100 μm is dispersed and mixed in an adhesive base including a styrene-isoprene-styrene block copolymer, an alicyclic saturated hydrocarbon resin, a softener, and diethyl sebacate, and does not contain L-menthol.

Specifically, the present invention is a felbinac-containing external patch wherein 0.1 to 10% by weight of felbinac having an average particle diameter of 5 μm or more and less than 100 μm is dispersed and mixed in an adhesive base which contains 10 to 30% by weight of a styrene-isoprene-styrene block copolymer, 10 to 50% by weight of an alicyclic saturated hydrocarbon resin, 10 to 75% by weight of a softener, and 0.1 to 10% by weight of diethyl sebacate, and does not contain L-menthol.

Effects of the Invention

The present invention can provide a felbinac-containing percutaneous absorption preparation, and in particular a felbinac-containing external patch which exhibits excellent drug release properties, low skin irritation, and high drug stability.

The felbinac-containing external patch provided by the present invention is useful for prevention and medical treatment for osteoarthritis, rheumatoid arthritis, low back pain, shoulder periarthritis, tendovaginitis, peritendinitis, lateral humeral epicondylitis (e.g., tennis elbow), myalgia, and swelling and pain after trauma by excellent anti-inflammatory analgesic effect of felbinac.

EMBODIMENTS FOR CARRYING OUT THE INVENTION

As described above, the basic aspect of the present invention is a felbinac-containing external patch wherein felbinac having an average particle diameter of 5 μm or more and less than 100 μm is dispersed and mixed in an adhesive base including a styrene-isoprene-styrene block copolymer, an alicyclic saturated hydrocarbon resin, a softener, and diethyl sebacate, and does not contain L-menthol.

Therefore, in the present invention felbinac serves as an active ingredient, and in particular felbinac having an average particle diameter of 5 μm or more and less than 100 μm is used as an active ingredient and dispersed in an adhesive base layer.

In the present invention, the amount of the felbinac added as an active ingredient in the preparation is not particularly limited as long as a preparation can be produced. The amount is preferably 0.1 to 10% by weight, and more preferably 0.5 to 6% by weight, relative to the weight of adhesive.

When the amount of the felbinac added in the adhesive is less than 0.1% by weight, the percutaneous absorption properties are insufficient, and the effect is not recognized. When it is more than 10% by weight, the effect is not further enhanced and it is not economic. Therefore, this is not preferable.

In consideration of dispersibility in an adhesive and workability in a production process, the felbinac added in the preparation preferably has an average particle diameter of 5 μm or more and less than 100 μm, more preferably 10 μm or more and less than 70 μm, and particularly preferably 15 μm or more and less than 40 μm.

When the average particle diameter is less than 5 μm, felbinac as an active pharmaceutical ingredient is subjected to secondary aggregation in the production process, and as result, felbinac may not be uniformly dispersed. Thus, the percutaneous absorption properties of a drug may deteriorate. In contrast, when it is 100 μm or more, the drug may not be uniformly dispersed in the adhesive. In particular, felbinac having a large particle diameter has low percutaneous absorption properties of a drug, and additionally an undesired influence in the production process, and in particular, a process of applying an adhesive to a release film. Therefore, aggregation of felbinac as an active pharmaceutical ingredient during the production may roughen the surface of the adhesive.

The styrene-isoprene-styrene block copolymer (hereinafter sometimes abbreviated to SIS) added in the present invention is a synthetic rubber which is a basic structure of an adhesive. The amount of the SIS added is in a range of 10 to 30% by weight, and preferably 10 to 20% by weight. When the amount of the added SIS is less than 10% by weight, the cohesion strength of the adhesive is decreased. In contrast, when it is more than 30% by weight, the adhesion and the workability during the production are lowered.

In the present invention, an alicyclic saturated hydrocarbon resin is preferably used as a tackifying resin in consideration of safety for the skin. Examples of such an alicyclic saturated hydrocarbon resin may include ARKON P90, P100, and P115 (manufactured by Arakawa Chemical Industries, Ltd.).

The amount of the alicyclic saturated hydrocarbon resin added is not particularly limited as long as a preparation can be produced. The added amount is preferably in a range of 10 to 50% by weight relative to the weight of adhesive.

When the content of alicyclic saturated hydrocarbon resin in the adhesive is less than 10% by weight, the adhesion is low. When it is more than 50% by weight, the adhesion of the preparation is high, causing a problem of pain when the preparation is peeled off.

Diethyl sebacate used in the present invention acts as a skin absorption enhancer of felbinac. The amount of the diethyl sebacate added is not particularly limited as long as a preparation can be produced. The added amount is preferably in a range of 0.1 to 10% by weight, and more preferably 1 to 7% by weight, relative to the weight of adhesive.

When the amount of the diethyl sebacate added in the adhesive is less than 0.1% by weight, skin permeability of felbinac is insufficient. When it is more than 10% by weight, problems such as skin irritation are caused. Therefore, this is not preferable.

In the present invention, it is found that the mixing ratio of felbinac to diethyl sebacate is a factor important for percutaneous absorption properties. Further, the ratio of felbinac to diethyl sebacate, represented by % by weight, is preferably in a range of 1:0.1 to 1:15, and more preferably 1:0.5 to 1:10.

When the mixing ratio is less than 1:0.1, the absorption enhancing effect due to diethyl sebacate cannot be obtained, and the drug absorption cannot be sufficiently obtained. When it is more than 1:15, felbinac is dissolved in excess diethyl sebacate, and the drug stability of a preparation is low.

The softener added in the present invention imparts softness to an adhesive. Examples thereof may include liquid rubber such as liquid polybutene, liquid polyisoprene, and liquid polyisobutylene; paraffin oil such as liquid paraffin; fatty acid esters such as isopropyl myristate and diisopropyl adipate; higher alcohols such as octyldodecanol; silicone oil; lanolin; squalane; squalene; and castor oil. Liquid polybutene and liquid paraffin are preferable.

The amount of the softener added is preferably in a range of 10 to 75% by weight, more preferably 15 to 60% by weight, and further preferably 20 to 50% by weight, relative to the weight of adhesive.

Further, various base ingredients used for a usual external patch can be used for the external patch of the present invention as long as they do not affect the other components. Such base ingredients are not particularly limited, and examples thereof may include rubber-based elastomers such as a styrene-butadiene-styrene block copolymer, styrene-butadiene rubber, natural rubber, and isoprene rubber, hydrophobic polymers such as polyacrylic acid-based polymer and silicone rubber; antioxidants such as dibutyl hydroxy toluene, pentaerythrityl-tetrakis[3-(3,5-di-tert-butyl-4-hydroxyphenyl)propionate], and tocopherol acetate, and inorganic fillers such as aluminum hydroxide, hydrated aluminum silicate, titanium oxide, zinc oxide, silicic anhydride, and magnesium silicate. If necessary, an absorption enhancer, a preservative, a refreshing agent, a disinfectant, a flavoring agent, and a coloring agent can be added.

Various supports used for the usual external preparation can be used for a support of the patch of the present invention as long as they do not affect the other components. Such supports are not particularly limited, and a laminate of a porous body of polyethylene, polypropylene, polyvinyl chloride, polyester, nylon, polyurethane and rayon, foam, a woven fabric, and a nonwoven fabric is used.

Various release liners used for the usual external preparation can be used for a release liner used for the patch of the present invention as long as they do not affect the other components. Such a release liner is not particularly limited. For example, a polyethylene terephthalate film, a polypropylene film, or paper can be used. In particular, a polyethylene terephthalate film is preferable. The release liner may be subjected to silicone treatment, if necessary, so that the release force from the adhesive layer is appropriate.

The external patch provided by the present invention can be produced as follows, for example.

SIS, a softener, and an alicyclic saturated hydrocarbon resin, constituting an adhesive layer, and an antioxidant are heated and dissolved. Subsequently, felbinac as an active ingredients and diethyl sebacate are added to the adhesive base, and the mixture is stirred and mixed, to prepare an adhesive in the patch.

The prepared adhesive (paste) is applied to the silicone-treated polyethylene terephthalate film to form an adhesive layer having a thickness of 50 to 300 μm. A polyester woven fabric or non-woven fabric as a support is laminated on the obtained adhesive layer, and the laminate is cut into appropriate size and shape, to obtain the external patch of the present invention.

EXAMPLES

Hereinafter, the present invention will be specifically described in detail with reference to Examples. However, the present invention is not limited to these examples.

In each Table in Examples and Comparative Examples, the amount of added component is represented by % by weight unless otherwise specified.

Example 1

SIS, polybutene, liquid paraffin, and dibutyl hydroxy toluene were kneaded under a heating condition of 170° C. and dissolved. Then, an alicyclic saturated hydrocarbon resin was added, and the mixture was kneaded under a heating condition of 130° C. and mixed to prepare an adhesive base.

Separately, felbinac having an average particle diameter of 5 μm or more and less than 100 μm was uniformly dispersed in a mixing liquid of diethyl sebacate and an appropriate amount of liquid paraffin under stirring to prepare a felbinac dispersion solution. The felbinac dispersion solution was added to the adhesive base, and the mixture was kneaded until the felbinac was uniformly dispersed, to prepare an adhesive. The adhesive was spread to a silicone-treated polyethylene terephthalate film so that the thickness was 100 μm, and a polyester woven fabric was laminated thereon to obtain a test preparation.

Examples 2 to 16

Each target patch of the present invention was produced from component compositions shown in Tables 1 to 3 in the same manner as in Example 1.

TABLE 1

| Component | Example | | | | |
|---|---|---|---|---|---|
| | 1 | 2 | 3 | 4 | 5 |
| SIS | 15 | 17 | 20 | 12 | 25 |
| Polybutene | 5 | 10 | 8 | 4 | 10 |
| Liquid Paraffin | 36 | 40 | 33.5 | 35 | 39 |
| Dibutylhydroxytoluene | 1 | 1 | 1 | 1 | 1 |
| Alicyclic Saturated hydrocarbon Resin | 35 | 25 | 30 | 45 | 15 |
| Felbinac | 4 | 5 | 0.5 | 2 | 3 |
| Diethyl Sebacate | 4 | 2 | 7 | 1 | 7 |
| Average Particle Diameter of Felbinac (μm) | 30 | 30 | 30 | 30 | 30 |

TABLE 2

| Component | Example | | | | |
|---|---|---|---|---|---|
| | 6 | 7 | 8 | 9 | 10 |
| SIS | 20 | 15 | 20 | 13 | 16 |
| Polybutene | 15 | 6 | 9 | 2 | 4 |
| Liquid Paraffin | 20 | 34 | 36 | 35 | 34.5 |
| Dibutylhydroxytoluene | 1 | 2 | 2 | 2 | 0.5 |
| Alicyclic Saturated hydrocarbon Resin | 40 | 37 | 20 | 42 | 37 |
| Felbinac | 1 | 3 | 6 | 2 | 5 |
| Diethyl Sebacate | 3 | 3 | 7 | 4 | 3 |
| Average Particle Diameter of Felbinac (μm) | 30 | 30 | 30 | 30 | 30 |

TABLE 3

| Component | Example 11 | 12 | 13 | 14 | 15 | 16 |
|---|---|---|---|---|---|---|
| SIS | 30 | 10 | 26 | 18 | 14 | 15 |
| Polybutene | 4 | 3 | 3 | 6 | 7 | 5 |
| Liquid Paraffin | 37 | 28 | 50 | 33.5 | 33 | 36 |
| Dibutylhydroxytoluene | 1 | 2 | 0.5 | 2 | 1 | 1 |
| Alicyclic Saturated Hydrocarbon Resin | 20 | 50 | 15 | 33 | 38 | 35 |
| Felbinac | 2 | 6 | 5 | 3.5 | 3.5 | 4 |
| Diethyl Sebacate | 6 | 1 | 0.5 | 4 | 3.5 | 4 |
| Averge Particle Diameter of Felbinac (μm) | 30 | 30 | 30 | 30 | 30 | 18 |

Comparative Examples 1 to 7

Each external patch of Comparative Examples was produced in the same manner as in Example 1 except that component compositions shown in Table 4 were used.

In the preparation of Comparative Example 7, felbinac as an active pharmaceutical ingredient was aggregated during the production (preparation of adhesive), and as a result, the preparation had an uneven surface. For this reason, the preparation was not subjected to the following preparation evaluation tests.

TABLE 4

| Component | Comparative Example 1 | 2 | 3 | 4 | 5 | 6 | 7 |
|---|---|---|---|---|---|---|---|
| SIS | 18 | 20 | 15 | 15 | 20 | 15 | 15 |
| Polybutene | 5 | 5 | 5 | 5 | 5 | 5 | 5 |
| Liquid Paraffin | 30 | 35 | 36 | 36 | 35 | 36 | 36 |
| Dibutylhydroxytoluene | 1 | 1 | 1 | 1 | 1 | 1 | 1 |
| Alicyclic Saturated Hydrocarbon Resin | | | 35 | 35 | 30 | 35 | 35 |
| Rosin Ester Derivative | 35 | 30 | | | | | |
| Felbinac | 4 | 2 | 4 | 4 | 2 | 4 | 4 |
| Diethyl Sebacate | 4 | | | | | 4 | 4 |
| Crotamiton | | 4 | | | 4 | | |
| Isopropyl Myristate | | | | 4 | | | |
| Disopropyl adipate | | | | 4 | | | |
| L-Menthol | 3 | 3 | | | 3 | | |
| Average Particle Diameter of Felbinac (μm) | 30 | 30 | 30 | 30 | 30 | 3 | 100 |

Test Example 1

Skin Primary Irritation Test on Humans (Human Patch Test)

The preparations in Examples 1 and 2 and Comparative Examples 1 and 2 were each punched to a diameter φ of 25 mm. Each preparation was applied to the inside of the upper arm in 15 healthy men for 24 hours. One hour and 24 hours after peeling off the preparation, skin irritation was judged. The results are shown in Table 5 below.

TABLE 5

| Test Preparation | Number of Person who had Skin irritation at applied site | |
|---|---|---|
| | 1 hr. after Peeling Off | 24 hrs. after Peeling Off |
| Example 1 | 0/15 | 0/15 |
| Example 2 | 0/15 | 0/15 |
| Comparative Example 1 | 3/15 | 2/15 |
| Comparative Example 2 | 4/15 | 3/15 |

As shown from the results in Table 5, the preparations in Examples 1 and 2 which are each the external patch of the present invention have low skin irritation as compared with Comparative Examples 1 and 2.

Test Example 2

Measurement of Amount of Felbinac Remaining in Used Patches

The preparations in Example 1 and Comparative Examples 3 and 4 were each punched to 5 cm×7 cm. Each preparation was applied to the back in 6 healthy men for 12 hours. A drug remained in each of the collected preparations was extracted and the amount of the drug was measured by HPLC.

The amount of the drug disappeared was calculated by subtracting the amount of drug remained from the amount of drug just before application. The results are shown in Table 6 below.

TABLE 6

| Test Preparation | Mount of Drug (Felbinac) Disappeared from Preparation 12 hrs after Application (Mean of 6 Persons) |
|---|---|
| Example 1 | 1.47 mg |
| Comparative Example 3 | 0.96 mg |
| Comparative Example 4 | 0.73 mg |

As shown from the results in Table 6, the preparation in Example 1 which is the patch of the present invention has a larger amount of drug disappeared and higher percutaneous absorption properties as compared with Comparative Examples 3 and 4.

Test Example 3

Stability Test

Samples (7 cm×10 cm) in Example 1 and Comparative Examples 2 and 5 were stored at 40° C. for 3 months. After then, the drug in each of the test preparations was extracted and the felbinac content was measured.

The felbinac content was compared with the felbinac content of each sample before the test (initial value). From the comparison, a percentage relative to the initial value (%) was calculated. The results are shown in Table 7.

TABLE 7

| Test Preparation | After Storage at 40° C. for 3 months (Relative to Initial Value) |
|---|---|
| Example 1 | 99.5% |
| Comparative Example 2 | 96.5% |
| Comparative Example 5 | 97.8% |

As shown from the results in Table 7, Example 1 which is the external patch of the present invention has excellent drug stability as compared with Comparative Examples 2 and 5.

Test Example 4

Release Test of Felbinac (Active Ingredient)

The preparations in Examples 1 and 16 and Comparative Example 6 were each punched to a diameter φ of 20 mm, and attached to the inside of a 100-mL beaker with a double sided tape so that the adhesive side faced the inside of the beaker.

The position of attached preparation was adjusted so that the lowest end of the preparation was located about 30 mm from the bottom of the beaker. After then, 100 mL of release solution (PBS buffer solution) was poured into the beaker, and was stirred with a magnetic stirrer. Ninety minutes after initiation of test, the felbinac content in the release solution was measured by high performance liquid chromatograph, and the release rate of Felbinac (active ingredient) was calculated. The results are shown in Table 8.

TABLE 8

| Test Preparation | Release Rate 90 min after beginning of Test (UNIT: %) |
|---|---|
| Example 1 | 95.8 |
| Example 16 | 76.5 |
| Comparative Example 6 | 47.9 |

As shown from the results in Table 8, Examples 1 and 16 which are the external patch of the present invention have very excellent release properties of Felbinac (active ingredient) as compared with the preparation in Comparative Example 6.

INDUSTRIAL APPLICABILITY

The present invention provides a felbinac-containing anti-inflammatory analgesic external patch which exhibits good drug release properties, low skin irritation, and high drug stability.

The external patch of the present invention is useful for prevention and medical treatment for osteoarthritis, rheumatoid arthritis, low back pain, shoulder periarthritis, tendovaginitis, peritendinitis, lateral humeral epicondylitis (e.g., tennis elbow), myalgia, and swelling and pain after trauma, and is widely applied.

The invention claimed is:

1. A felbinac-containing external patch wherein 0.1 to 10% by weight of felbinac, having an average particle diameter of 5 μm or more and less than 100 μm, is dispersed and mixed in an adhesive base comprising:
    10 to 30% by weight of a styrene-isoprene-styrene block copolymer,
    10 to 50% by weight of an alicyclic saturated hydrocarbon resin,
    10 to 75% by weight of a softener, and
    0.1 to 10% by weight of diethyl sebacate,
    wherein the patch does not contain L-menthol, wherein the weight ratio of felbinac to diethyl sebacate is in the range of 1:0.1 to 1:15, and wherein the % by weight of said components are relative to the weight of the adhesive base.

* * * * *